US011191516B2

(12) United States Patent
Mirzaei et al.

(10) Patent No.: US 11,191,516 B2
(45) Date of Patent: Dec. 7, 2021

(54) SYSTEMS AND METHODS FOR POWERING AN IMAGING SYSTEM (71) Applicant: GE Precision Healthcare LLC, Milwaukee, WI (US)

(72) Inventors: Saeid Mirzaei, Muskego, WI (US); Eric Aasen, Pewaukee, WI (US); Todd Filtz, Hartland, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

(21) Appl. No.: 16/576,421

(22) Filed: Sep. 19, 2019

(65) Prior Publication Data
US 2021/0085277 A1    Mar. 25, 2021

(51) Int. Cl.
*A61B 6/00* (2006.01)
*H05G 1/18* (2006.01)
*H05G 1/48* (2006.01)
*A61B 6/03* (2006.01)

(52) U.S. Cl.
CPC .............. *A61B 6/56* (2013.01); *A61B 6/4488* (2013.01); *A61B 6/54* (2013.01); *H05G 1/18* (2013.01); *H05G 1/48* (2013.01); *A61B 6/032* (2013.01)

(58) Field of Classification Search
None
See application file for complete search history.

(56) References Cited

U.S. PATENT DOCUMENTS

| 5,808,376 | A | 9/1998 | Gordon et al. |
| 7,522,705 | B2 | 4/2009 | Katcha et al. |
| 9,084,335 | B2 | 7/2015 | Mekonnen et al. |
| 10,067,203 | B2 | 9/2018 | Ganesh et al. |
| 10,620,281 | B2 * | 4/2020 | Kanakasabai ............ A61B 6/56 |
| 10,622,815 | B2 * | 4/2020 | Depond ................ H02J 7/0016 |
| 10,703,356 | B2 * | 7/2020 | Lacroix ................. B60W 10/08 |
| 2008/0112537 | A1 * | 5/2008 | Katcha ...................... A61B 6/56 378/102 |
| 2011/0302432 | A1 | 12/2011 | Harris et al. |
| 2017/0102441 | A1 * | 4/2017 | Ganesh .................. G01R 33/36 |

(Continued)

OTHER PUBLICATIONS

Hamidi, S. et al., "Design and Implementation of a DC Line-Interactive Uninterruptible Power Supply (UPS) with Load Leveling," Proceedings of the IEEE Energy Conversion Congress & Expo, Sep. 20, 2015, Montreal, Canada, 1 page.

*Primary Examiner* — Thomas R Artman (57) ABSTRACT

Methods and systems are provided for powering an imaging system. In one embodiment, a system comprises a direct current (DC) bus, an x-ray source coupled to the DC bus, a power distribution unit (PDU) with an input coupled to a three-phase alternating current (AC) source and an output coupled to the DC bus, and an energy storage apparatus comprising a supercapacitor, the energy storage apparatus coupled to the DC bus and configured to store electrical energy output by the PDU in the supercapacitor, and output the stored electrical energy directly to the DC bus for powering the x-ray source. In this way, an x-ray source of an imaging system may be adequately powered beyond the limitations of a PDU without upgrading the electrical utilities of a hospital and without upgrading the PDU. The supercapacitor is protected by FPGA by measuring input current, voltage, temperature, and voltage balance.

16 Claims, 8 Drawing Sheets (56) References Cited

U.S. PATENT DOCUMENTS

2017/0285119 A1* 10/2017 Kanakasabai ...... G01R 33/3614
2019/0256079 A1*  8/2019 Lacroix ................... B60K 6/28
2019/0280490 A1*  9/2019 Depond ................. B60L 53/55
2020/0276967 A1*  9/2020 Lacroix ............... F02N 11/0814
2021/0085277 A1*  3/2021 Mirzaei ................... H05G 1/18

* cited by examiner

SYSTEMS AND METHODS FOR POWERING AN IMAGING SYSTEM

FIELD

Embodiments of the subject matter disclosed herein relate to medical imaging systems, and more particularly, to addressing the power requirements of a computed tomography (CT) imaging system.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

BRIEF DESCRIPTION

In one embodiment, a system comprises a direct current (DC) bus, an x-ray source coupled to the DC bus, a power distribution unit (PDU) with an input coupled to a three-phase alternating current (AC) source and an output coupled to the DC bus, and an energy storage apparatus comprising a supercapacitor, the energy storage apparatus coupled to the DC bus and configured to store electrical energy output by the PDU in the supercapacitor, and output the stored electrical energy directly to the DC bus for powering the x-ray source. In this way, an x-ray source of an imaging system may be adequately powered beyond the limitations of a PDU without upgrading the electrical utilities of a hospital and without upgrading the PDU.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
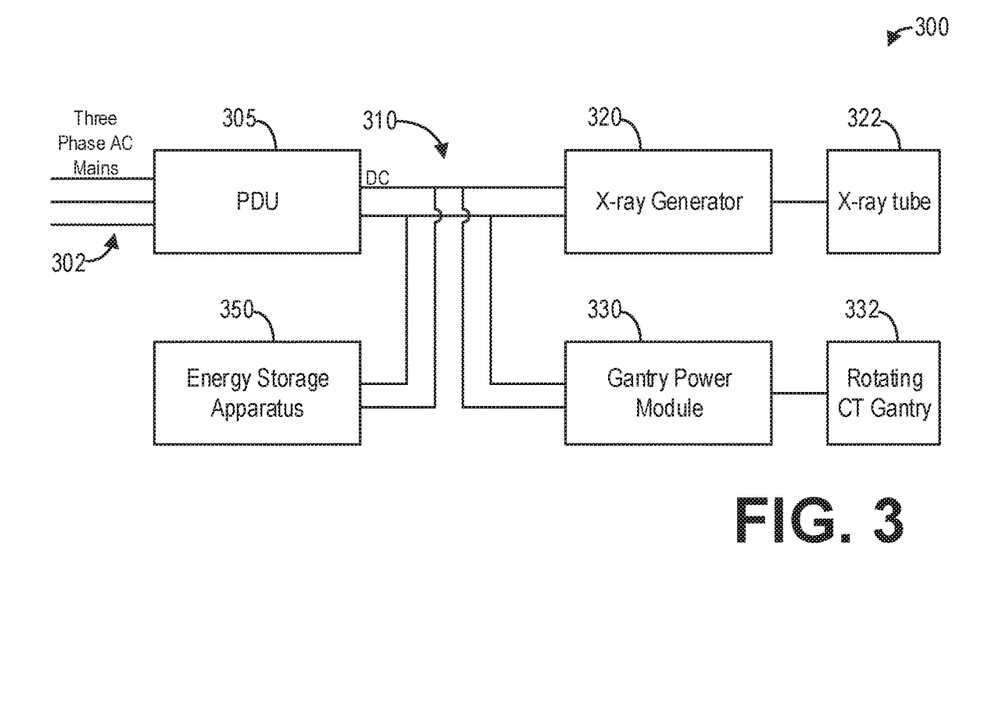
FIG. 3 shows a block schematic diagram of an example system for powering components of an imaging system with an energy storage apparatus according to an embodiment.
Figure 4:
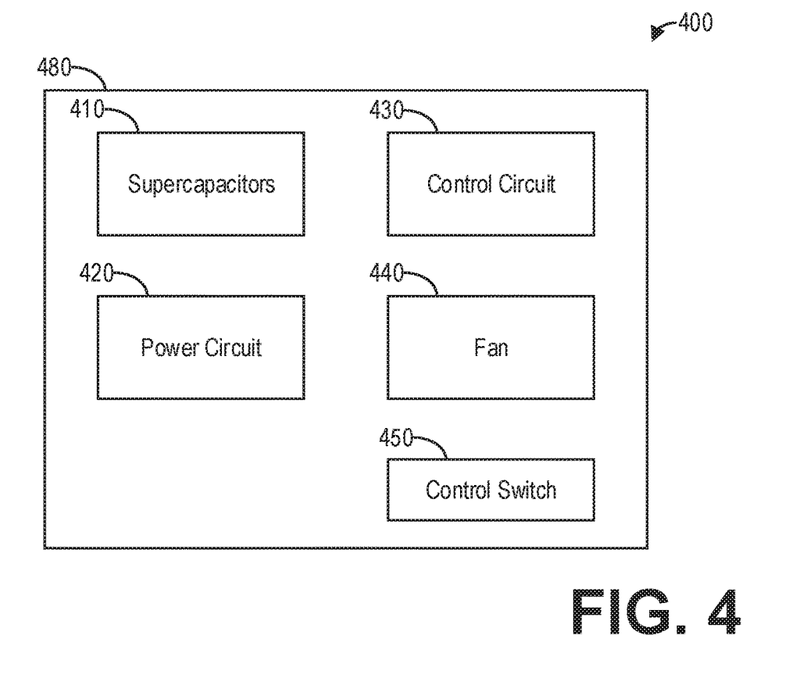
FIG. 4 shows a block diagram illustrating an example energy storage apparatus according to an embodiment.
Figure 5:
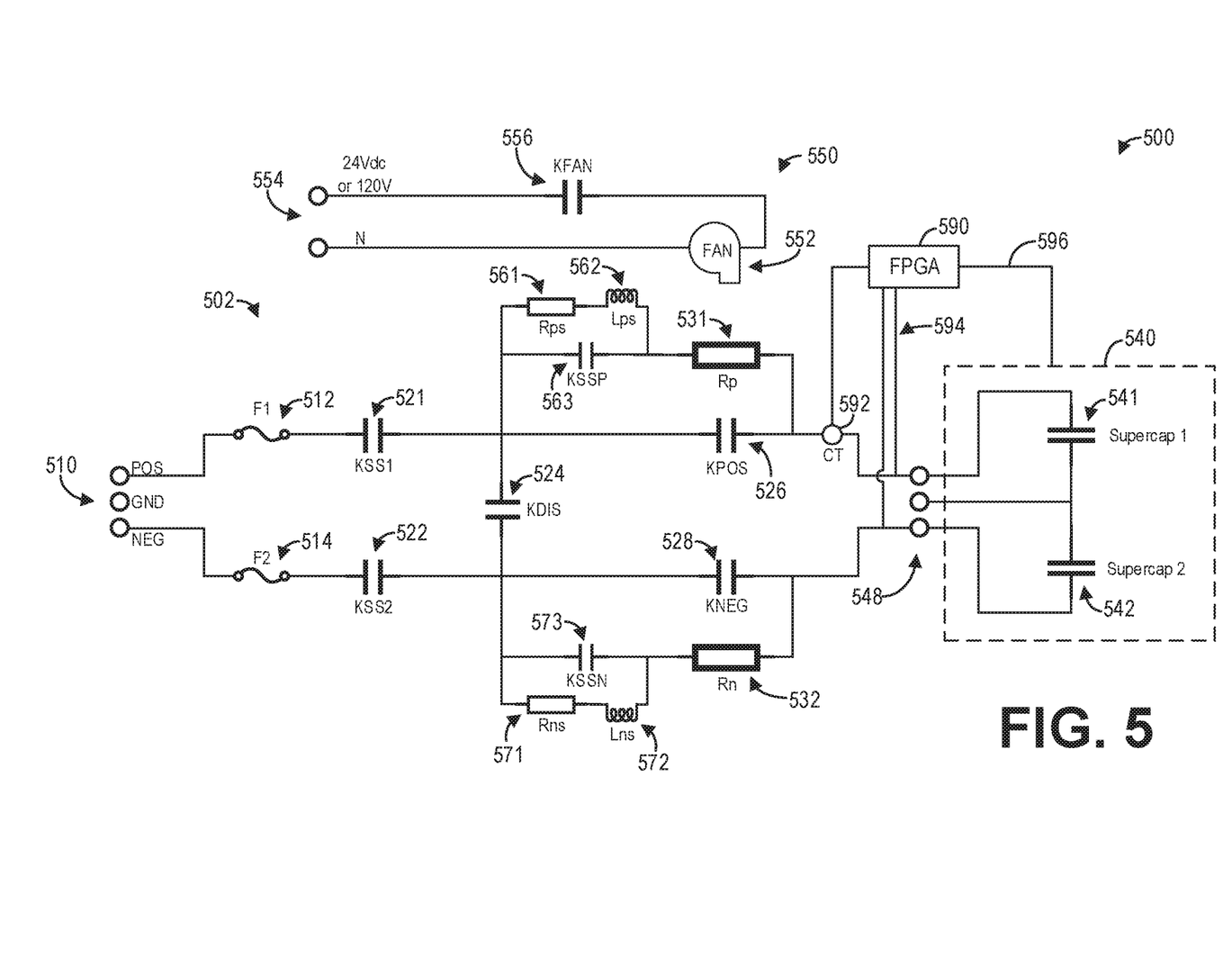
FIG. 5 shows a schematic for an example control circuit for an energy storage apparatus according to an embodiment.
Figure 6:
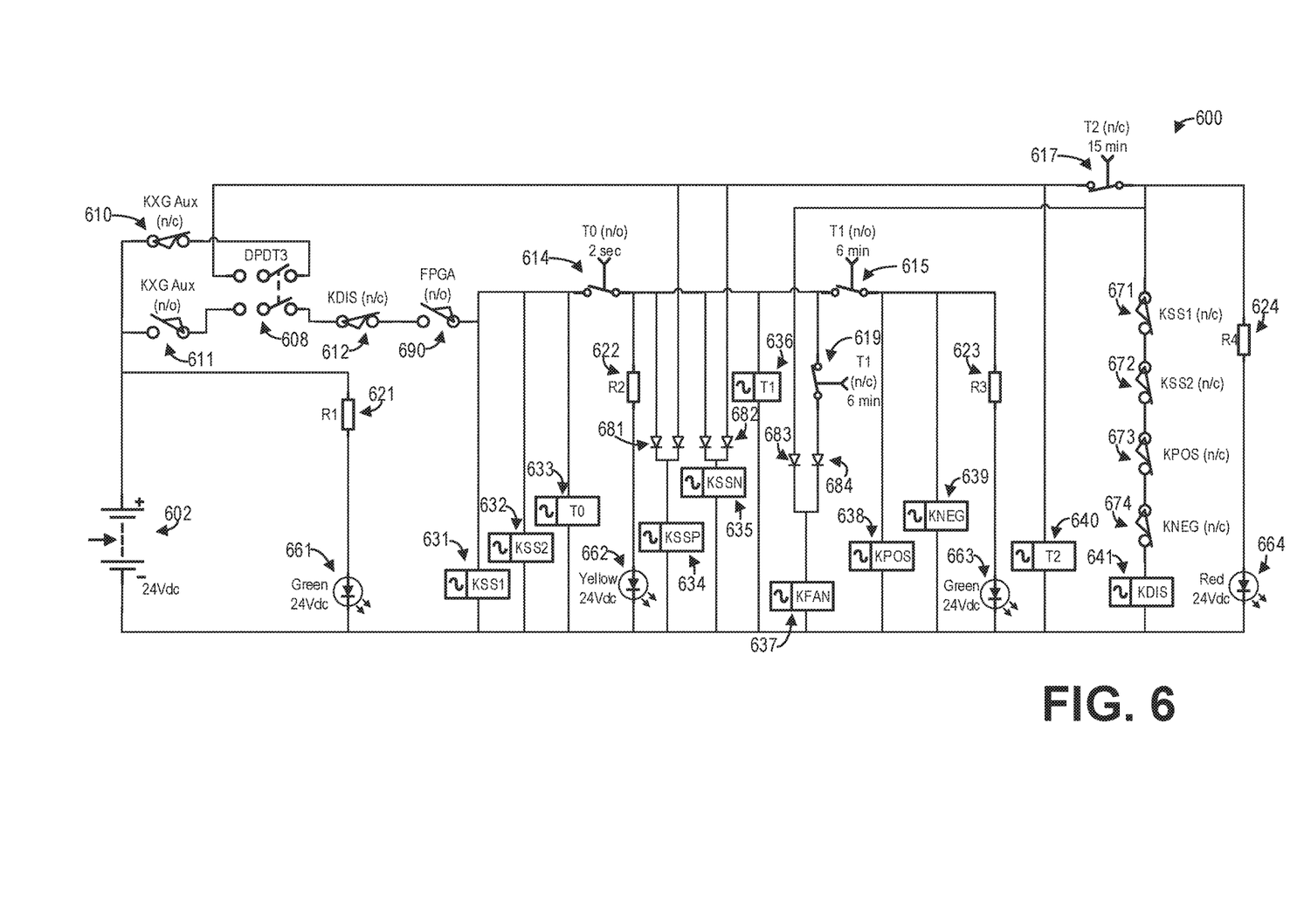
FIG. 6 shows a schematic for an example power circuit for an energy storage apparatus according to an embodiment.
Figure 7:
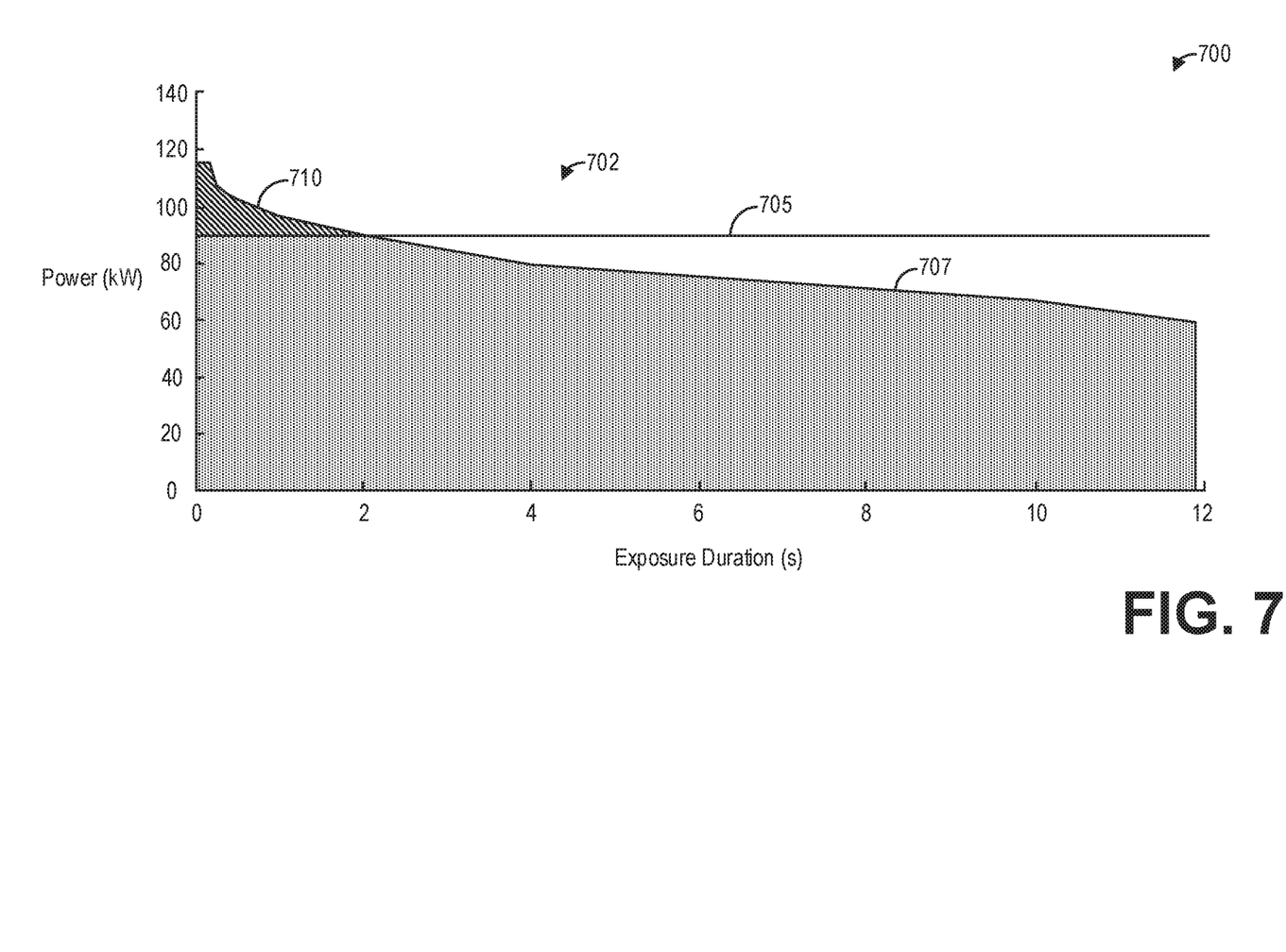
FIG. 7 shows a graph illustrating an example power consumption for an x-ray tube of an imaging system according to an embodiment.
Figure 8:
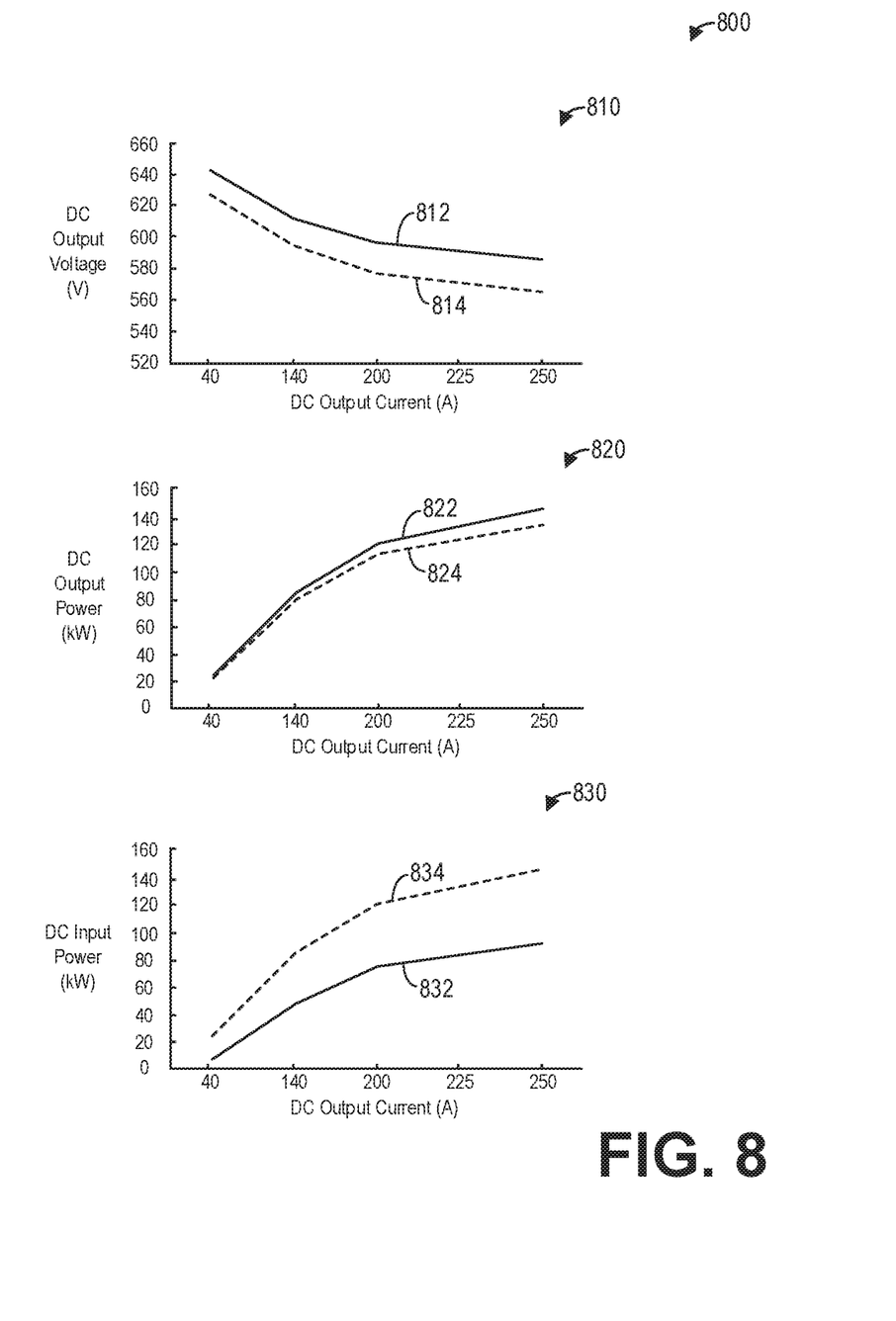
FIG. 8 shows a set of graphs illustrating an example power performance of a power distribution unit configured with an energy storage apparatus in contrast to a power distribution unit configured without an energy storage apparatus according to an embodiment.
Figure 9:
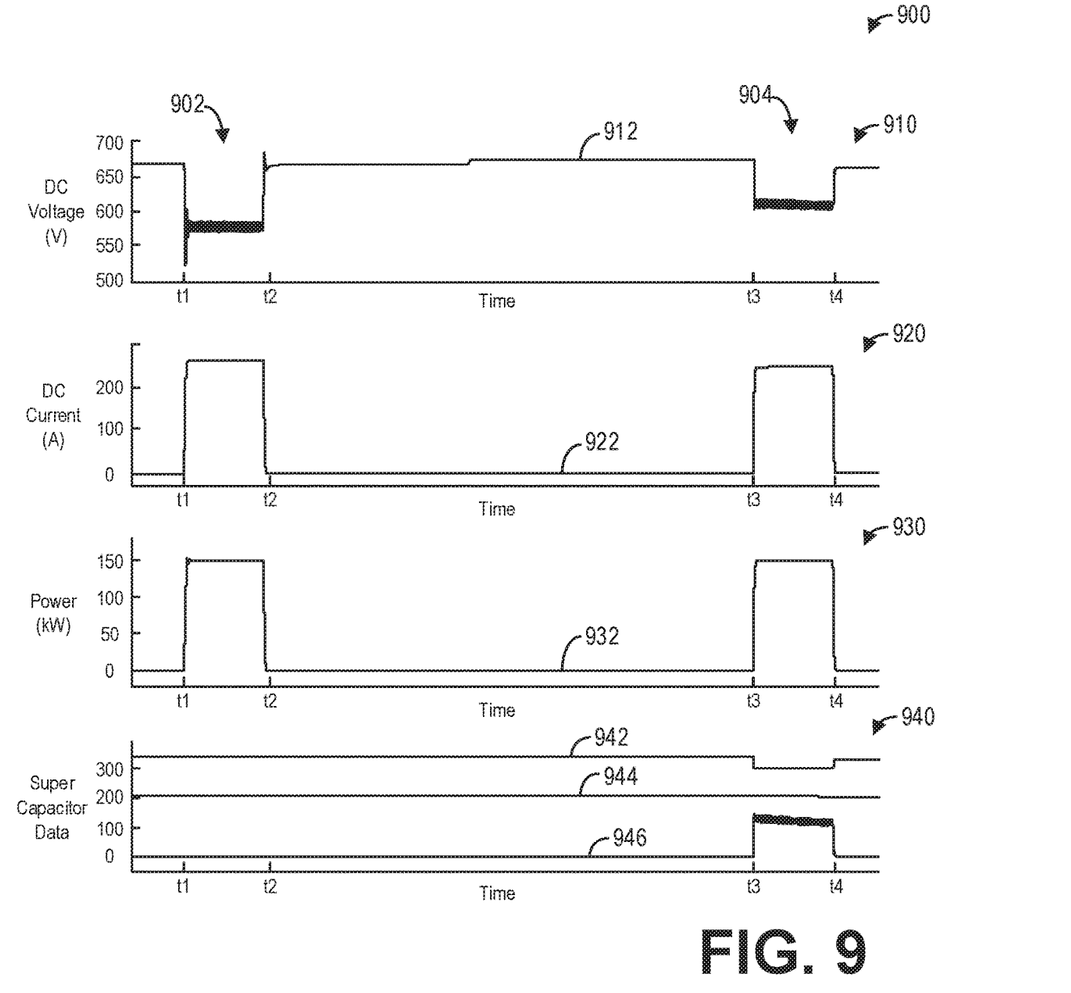
FIG. 9 shows a set of graphs illustrating example electrical measurements for exposures with and without an energy storage apparatus according to an embodiment.

The following description relates to various embodiments of medical imaging systems. In particular, systems and methods are provided for powering computed tomography (CT) imaging systems. An example of a CT imaging system that may be used to acquire images in accordance with the present techniques is provided in FIGS. 1 and 2. The CT imaging system may include at least one x-ray tube that consumes a large amount of energy when operated in certain imaging modes. In some instances, the power requirements of a CT imaging system including such an x-ray tube may exceed the power capacity for the electrical utilities of the building housing the CT imaging system and/or a power distribution unit (PDU) that transfers the alternating current (AC) of the electrical utilities to direct current (DC) for powering the CT imaging system. One approach to addressing the power requirements of the CT imaging system may include upgrading the utilities, such as by increasing the size of cables, fuses, circuit breakers, and/or a distribution transformer. Another approach may include upgrading to a larger PDU or installing a second PDU. However, such solutions may be costly and time-consuming to the point of discouraging upgrades to a CT imaging system. Another approach includes providing an energy storage device such as a supercapacitor module configured in parallel with a PDU, as shown in FIG. 3, to reduce peak load requirements of the input power line. A supercapacitor module may include one or more supercapacitors as well as a control circuit for controlling the supercapacitor module, a power circuit for powering components of the supercapacitor module, one or more fans for cooling components of the supercapacitor module, and a control switch for charging or discharging the supercapacitor module, as shown in FIGS. 4-6. The supercapacitor module as described herein may therefore provide power to one or more components of the CT imaging system during at least a portion of an exposure, as depicted in FIG. 7, to enable power consumption above the output limits of a PDU, as depicted in FIGS. 8 and 9. A method for controlling the supercapacitor module, such as the method depicted in FIG. 10, includes selectively charging or discharging the supercapacitors of the supercapacitor module based on the position of a control switch of the supercapacitor module.

It should be appreciated that, while the term energy storage apparatus is broadly used herein to refer to an apparatus comprising one or more supercapacitors for providing assistance in powering an imaging system, the energy storage apparatus described herein comprises a supercapacitor module and therefore the terms "energy storage apparatus" and "supercapacitor module" may be used interchangeably herein.

Though a CT system is described by way of example, it should be understood that the present techniques may also be useful when applied to other imaging modalities, such as MRI, C-arm angiography, and so forth. The present discussion of a CT imaging modality is provided merely as an example of one suitable imaging modality.

Figure 1:
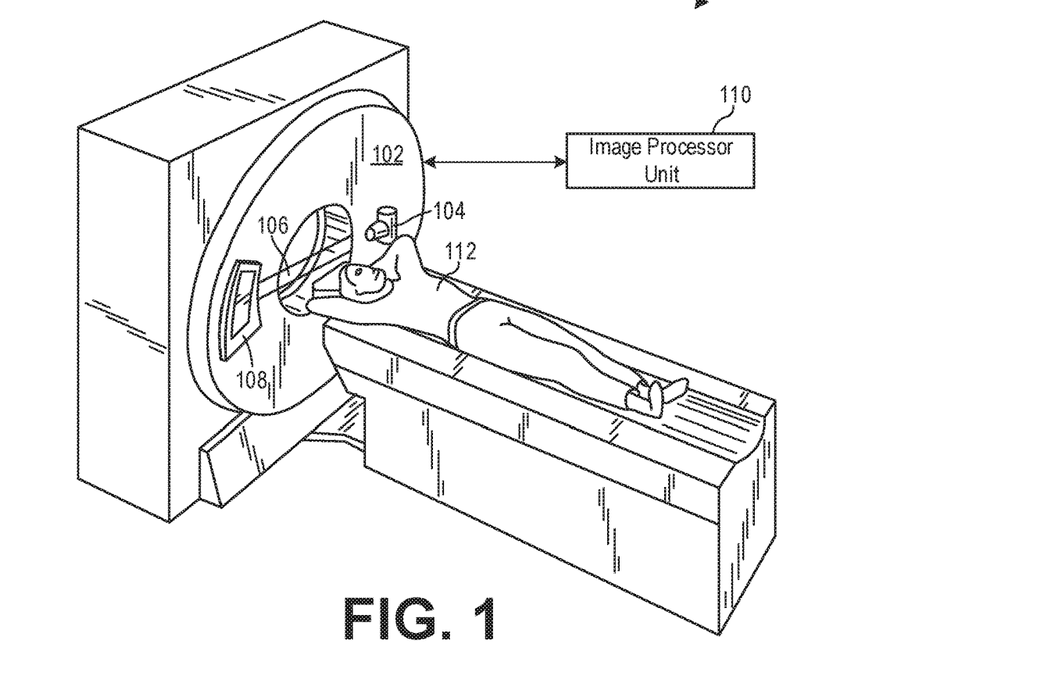
FIG. 1 shows a pictorial view of an imaging system according to an embodiment.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring projection data corresponding to the patient at different energy levels. In some embodiments, the x-ray source 104 may enable dual-energy gemstone spectral imaging (GSI) by rapid kVp switching. In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some known CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

The projection data is processed to reconstruct an image that corresponds to a two-dimensional slice taken through the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
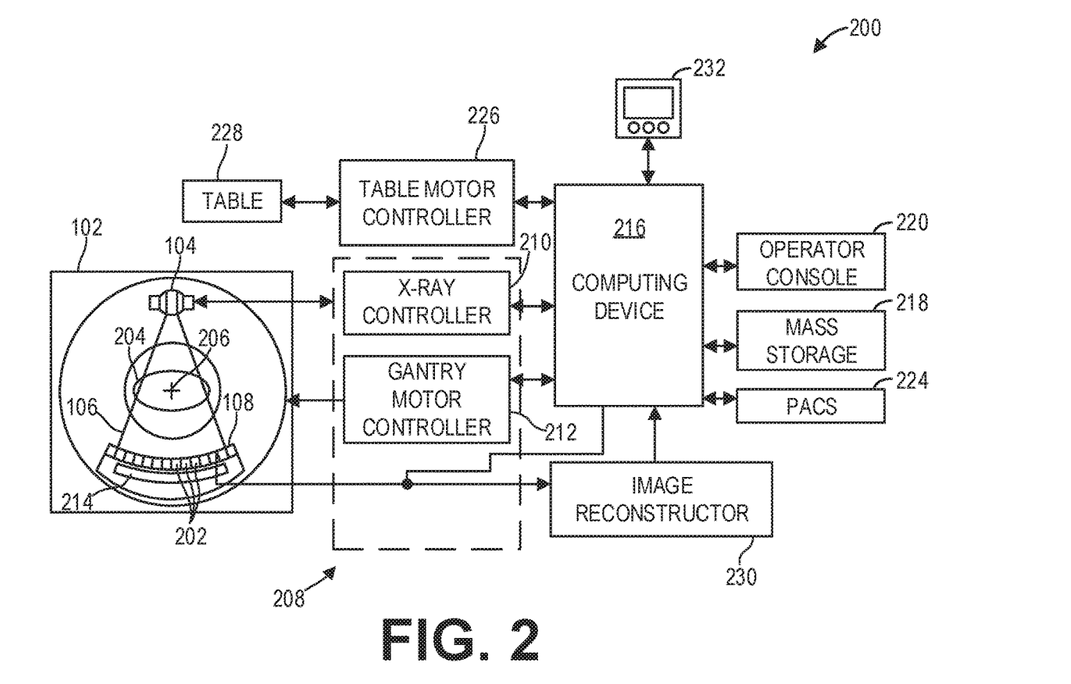
FIG. 2 shows a block schematic diagram of an exemplary imaging system according to an embodiment.

FIG. 2 illustrates an exemplary imaging system 200 similar to the CT system 100 of FIG. 1. In accordance with aspects of the present disclosure, the imaging system 200 is configured for imaging a subject 204. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may comprise photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

FIG. 3 shows a block schematic diagram of an example system 300 for powering components of an imaging system with an energy storage apparatus according to an embodiment. The system 300 comprises an imaging system electrical circuit that may be incorporated into the CT system 100 of FIG. 1 or the imaging system 200 of FIG. 2. System 300 includes a DC bus 310 connected to the DC output of a power distribution unit (PDU) 305. An AC input of the PDU 305 is coupled to a three-phase AC mains or AC electrical source 302.

A rotating CT gantry 332, which may comprise the gantry 102 of FIGS. 1 and 2, is mechanically coupled to a gantry power module 330, which may comprise or be integrated into the gantry motor controller 212 of FIG. 2. The DC bus 310 is coupled to the gantry power module 330 for powering the gantry power module 330 and thus the rotating CT gantry 332. In some examples, rotational energy in rotating the gantry is re-generatively converted to DC electrical energy in the gantry power module 330 during gantry braking, and the DC electrical energy may be provided to the DC bus 310.

An x-ray tube 322, which may comprise the x-ray source 104 of FIGS. 1 and 2, is coupled to an x-ray generator 320, which may comprise the x-ray controller 210 of FIG. 2. The DC bus 310 is coupled to the x-ray generator 320 for powering the x-ray generator 320 and thus the x-ray tube 322.

The system 300 further comprises an energy storage apparatus 350 configured in parallel to the PDU 305 via the DC bus 310. The energy storage apparatus 350 comprises a supercapacitor module as discussed further herein. The energy storage apparatus 350 stores energy output by the PDU 305 in one or more supercapacitors, and is configured to output the stored energy to at least the x-ray generator 320 for at least a portion of an exposure of the x-ray tube 322. While In this way, when the desired power consumption of components of the CT system 100 or the imaging system 200, such as the x-ray tube 322, exceeds the output power of the PDU 305, the energy storage apparatus 350 assists the PDU 305 in providing sufficient power for the desired power consumption.

As described further herein, the energy storage apparatus 350 is configured for fast charging as well as fast response, as the energy storage apparatus 350 is directly connected to the DC bus 310. Typically an energy storage apparatus includes a converter for controlling the voltage and current of supercapacitors; however, the energy storage apparatus 350 does not include such a converter. As the energy storage apparatus 350 does not include a converter for transferring DC power, there is no switching power loss and the efficiency of the energy storage apparatus 350 is improved relative to energy storage apparatuses that include converters. Further, by directly connecting the energy storage apparatus 350 to the DC bus 310, the x-ray generator 320 exhibits a lower DC voltage drop relative to systems without the energy storage apparatus 350, so that the output power of the x-ray generator 320 is higher. Further still, the x-ray generator 320 has a better and more stable performance when the input DC voltage is stable with low drop voltage.

FIG. 4 shows a block diagram illustrating an example energy storage apparatus or a supercapacitor module 400 according to an embodiment. The supercapacitor module 400 may be implemented in the systems of FIGS. 1-3 as the energy storage apparatus 350, for example. The supercapacitor module 400 comprises one or more supercapacitors 410, a power circuit 420 for powering components of the supercapacitor module 400, a control circuit 430 for controlling components of the supercapacitor module 400, at least one fan 440 for cooling one or more components of the supercapacitor module 400, and a control switch 450 for controlling operation of the supercapacitor module 400.

The supercapacitors 410 comprise supercapacitors or ultra-capacitors with capacitance values ranging from less than 3 Farad (F) to over 3,000 F. The number of supercapacitors 410 and the capacitance values of the supercapacitors 410 may be selected according to the power requirements of the imaging system 200 as well as the output capacity of the PDU 305. The supercapacitor module 400 may include, as an illustrative example, two supercapacitors 400 with capacitance values of 2.4 F, 700 Vdc for enabling the use of an upgraded x-ray tube such as x-ray tube 322 without upgrading the PDU 305. Example circuits for the supercapacitor module 400 with two supercapacitors, including example circuits for the power circuit 420 and the control circuit 430, are described further herein with regard to FIGS. 5 and 6.

The one or more fans 440 of the supercapacitor module 400 are configured to selectively cool one or more components of the supercapacitor module 400 that become heated during charging and/or discharging of the supercapacitors 410. For example, the one or more fans 440 may be oriented towards one or more resistors of the power circuit 420 and/or the control circuit 430, and may be configured to circulate air to and from the resistors during charging and/or discharging of the supercapacitors 410.

The control switch 450 may comprise a manual switch that is operable by a user such as an imaging technician or may comprise a relay that is automatically operable by the computing device 216 of the imaging system 200, for example. The control switch 450 may include at least three positions, including an Off position wherein current flow to and from the supercapacitor module 400 is disabled, a Charge position wherein the supercapacitors 410 are charged to capacity, and a Discharge position wherein the supercapacitors 410 are discharged so that the supercapacitor module 400 may be serviced, for example. The power circuit 420 and/or the control circuit 430 are configured to selectively charge and discharge the supercapacitors 410, as described further herein, and so the control switch 450 enables manual control of the power circuit 420 and/or the control circuit 430.

Further, the components of the supercapacitor module 400 may be housed in a housing 480, which may be specially adapted to simply installation of the supercapacitor module 400 with a PDU such as PDU 305. For example, the housing 480 may be configured such that the supercapacitor module 400 may be installed on top of the PDU 305, in some examples.

FIG. 5 shows a schematic for an example power circuit 500 for a supercapacitor module according to an embodiment. The power circuit 500 may be implemented as the power circuit 420 of the supercapacitor module 400, for example, or of the energy storage apparatus 350.

The power circuit 500 includes a primary power circuit 502. Electricity is provided to the primary power circuit 502 via the terminals 510, including a positive terminal, a negative terminal, and a ground terminal as depicted. For example, DC power from the DC bus 310 is provided to the primary power circuit 502 via the terminals 510.

The primary power circuit 502 further includes a first fuse (F1) 512 coupled to the positive terminal and a second fuse (F2) 514 connected to the negative terminal. Current flows from the positive (POS) and negative (NEG) terminals of the terminals 510 to the first fuse (F1) 512 and the second fuse (F2) 514, respectively. The primary power circuit 502 further includes a plurality of capacitors, including a DC Contactor 521 for the first soft start contactor (KSS1), a DC contactor 522 for the second soft start contactor (KSS2), a DC contactor 524 for the discharge contactor (KDIS), a DC contactor 526 for the positive contactor (KPOS), and a DC contactor 528 for the negative contactor (KNEG). The DC contactors 521 and 522 for the soft start contactors enable the soft starting of the charging of the supercapacitors 540.

The primary power circuit 502 further includes supercapacitors 540 including a first supercapacitor 541 and a second supercapacitor 542, as depicted, which couple to the remainder of the primary power circuit 502 via the terminals 548. Current flows from the terminals 510 to the supercapacitors 540 by passing through the capacitors once the corresponding contactors are closed. Each of the supercapacitors 541 and 542 may comprise at least 164 400 F, 2.7V super capacitors coupled in series, for example, to work under high DC voltage, such that the overall capacitance of each supercapacitor 541 and 542 is 2.4 F for 450 Vdc.

The primary power circuit 502 further includes a resistor (Rp) 531 positioned in parallel with the DC contactor 526 and a resistor (Rn) 532 positioned in parallel with the DC contactor 528. In line with the resistor (Rp) 531, the primary power circuit 502 further includes a resistor (Rps) 561 positioned in series with an inductor (Lps) 562, both of which are in parallel with a DC contactor (KSSP) 563. Similarly, in line with the resistor (Rn) 532, the primary power circuit 502 further includes a resistor (Rns) 571 in series with an inductor (Lns) 572, both of which are in parallel with a DC contactor (KSSN) 573. The configuration of the resistors 561 and 571, inductors 562 and 572, and contactors 563 and 573 on the positive and negative sides provide additional protection for the supercapacitors 540 in the case of an unexpected open circuit of the super capacitor 541 and 542. As an illustrative example, the resistors 561 and 571 may comprise 1000Ω resistors while the inductors 562 and 572 comprise 1 mH inductors to provide a delay time. For example, when the soft start contactors KSS1 and KSS2 are closed to charge the supercapacitors 540, but a supercapacitor leg is broken thereby creating an open circuit, then high DC voltage may damage the voltage balance circuit in the super capacitors 541 and 542.

The resistors 561 and 571 as well as the inductors 562 and 572 therefore provide a delay time while a field programmable gate array (FPGA) 590 evaluates the supercapacitors 540 to determine whether there is an open circuit, for example, by determining whether a jump voltage is present. If the circuit is properly closed, the soft start contactors bypass the resistors 561 and 571 as well as the inductors 562 and 572 after the maximum 2 second delay time. Otherwise, an FPGA relay opens to prevent current flow in the circuit as discussed further herein with regard to FIG. 6. To monitor and evaluate the state of the power circuit 502 and the supercapacitors 540, the FPGA 590 is coupled to a current transformer (CT) 592 to measure current of the circuit. The FPGA 590 further includes a voltage sensor 594 to measure the voltage of the circuit. The CT 592 and the voltage sensor 594 are provided at the terminals 548 of the supercapacitors 540 so that the FPGA 590 may monitor the input current and terminal voltage of the supercapacitors 540. The FPGA 590 is further coupled to sensors 596 provided at the supercapacitors 540 to measure the temperature and voltage balance of the supercapacitors 540. If the voltage of one capacitor in the supercapacitors 541 and 542 exceeds a threshold, such as 2.6 V, or if the temperature of one of the supercapacitors 541 and 542 exceeds a temperature threshold, such as 65 degrees Celsius, then the FPGA relay described further herein is immediately opened to protect the circuit.

The power circuit 500 further includes a fan circuit 550. The fan circuit 550 includes terminals 554 for providing electricity to the fan circuit 550, as well as a fan capacitor 552 and at least one fan 552. The at least one fan 552 depicted is directed towards the resistor 531, and is configured to circulate air and thus cool the resistor 531 during charging and discharging of the supercapacitors 540. It should be appreciated that a second fan configured similar to the at least one fan 552 may be provided for cooling the resistor 532 during charging and discharging.

FIG. 6 shows a schematic for an example control circuit 600 for a supercapacitor module according to an embodiment. The control circuit 600 may be implemented as the control circuit 430 of the supercapacitor module 400, for example, or of the energy storage apparatus 350.

The control circuit 600 includes a DC voltage source 602 which is coupled to the DC bus 310, for example. The control circuit 600 further includes a plurality of switches, including a switch 608, a switch 610, a switch 611, a switch 612, a switch 614 a switch 615, a switch 617, a switch 619, a switch 671, a switch 672, a switch 673, a switch 674, and an FPGA relay 690. The switch 608 comprises a double-pole double-throw (DPDT) switch with three positions, corresponding to Charge, Off, and Discharge. Accordingly, the position of the switch 608 determines whether the supercapacitors 410 of the supercapacitor module 400, for example, are charging (Charge) or discharging (Discharge) as well as whether current is discontinued (Off) throughout the supercapacitor module 400. The switch 610 comprises a KXG Aux switch that is normally closed (n/c), while the switch 611 comprises a KXG Aux switch that is normally open (n/o).

The switch 612 comprises a normally-closed (n/c) switch corresponding to the discharge contactor (KDIS). The switch 614 comprises a normally-open (n/o) timer switch (T0) configured for two seconds. The switch 615 comprises a normally-open (n/o) timer switch (T1) configured for six minutes, while the switch 619 comprises a normally-closed timer switch configured for six minutes. The switch 617 comprises a normally-closed timer switch (T2) configured for fifteen minutes, and is arranged in line with the discharge AC relay 638 for discharging the supercapacitors in fifteen minutes. The switch 671 comprises a normally-closed switch for the first soft start contactor (KSS1), the switch 672 comprises a normally-closed switch for the second soft start contactor (KSS2), the switch 673 comprises a normally-closed switch for the positive contactor (KPOS), and the switch 674 comprises a normally-closed switch for the negative contactor (KNEG).

As mentioned above, the field-programmable gate array (FPGA) of the supercapacitor module measures the supercapacitor current and voltage to determine if there is a jump voltage, which would indicate an open circuit. If the FPGA finds an open circuit on the supercapacitor, then the FPGA switch or relay 690 is configured to remain open to prevent current flow through the circuit. Otherwise, the FPGA switch 690 closes to allow current flow.

The control circuit 600 further includes a plurality of AC relays, including an AC relay 631 for the first soft start contactor (KSS1), an AC relay 632 for the second soft start contactor (KSS2), an AC relay 633 for the zeroth timer switch (T0), an AC relay 634 for the positive soft start contactor (KSSP), an AC relay 635 for the negative soft start contactor (KSSN), an AC relay 636 for the first timer switch (T1), an AC relay 637 for the fan contactor (KFAN), an AC relay 638 for the positive contactor (KPOS), an AC relay 639 for the negative contactor (KNEG), an AC relay 640 for the second timer switch (T2), and an AC relay 641 for the discharge contactor (KDIS). The control circuit 600 further includes a plurality of resistors, including a first resistor (R1) 621, a second resistor (R2) 622, a third resistor (R3) 623, and a fourth resistor (R4) 624.

The control circuit 600 further includes a plurality of light emitting diodes (LEDs), including a green LED 661 positioned in the control circuit 600 to indicate that the control circuit 600 is on, a yellow LED 662 positioned in the control circuit 600 to indicate that the supercapacitors 410 are charging, a green LED 663 positioned in the control circuit 600 to indicate that the supercapacitors 410 are charged, and a red LED 664 positioned in the control circuit 600 to indicate that the supercapacitors 410 are discharging.

The control circuit 600 further includes diodes including a first pair of diodes 681 for directing current flow from the discharge circuit and the charge circuit to the AC relay 634, as well as a second pair of diodes 682 for directing current from the discharge circuit and the charge circuit to the AC relay 635. The control circuit 600 further includes a diode 683 for directing current from the discharge circuit to the AC relay 637 for the fan as well as a diode 684 for directing current from the charge circuit to the AC relay 637, such that the one or more fans 440 may be activated to cool components of the supercapacitor module 400, for example, when the supercapacitors 410 are charging or discharging.

To illustrate how the energy storage apparatus or supercapacitor modules described herein, such as energy storage apparatus 350 or supercapacitor module 400, assists in achieving energy requirements for an imaging system, FIG. 7 shows a graph 700 illustrating an example power consumption 702 for an x-ray tube, such as the x-ray tube 322 or the x-ray source 104, of an imaging system, such as the imaging system 200, according to an embodiment. The graph 700 depicts power, measured in kilowatts (kW), as a function of exposure duration of the x-ray tube, measured in seconds (s). The output power limit 705 of a PDU, such as the PDU 305, for example, may be limited to 90 kW, as an illustrative and non-limiting example. The shaded areas of the graph 700 depict the power consumption 702 of the x-ray tube over time.

As depicted, the power consumption 702 of the x-ray tube decreases as the duration of an exposure increases. As the PDU is capable of providing power up to the output power limit 705, the area 707 of the power consumption 702 is provided by the PDU. However, initially during an exposure, the power consumption 702 may exceed the output power limit 705 of the PDU. For example, as depicted, the power consumption 702 exceeds the output power limit 705 for the first two seconds of an exposure. The power corresponding to the area 710 is therefore provided by the supercapacitors of a supercapacitor module as described hereinabove. Given that the power consumption 702 may initially exceed the output power limit 702, the response speed of the supercapacitor module should be fast so that the additional power 710 may be provided when needed. The supercapacitor module described herein achieves the fast response necessary for providing such additional power.

FIG. 8 shows a set of graphs 800 illustrating an example power performance of a PDU, such as the PDU 305, with and without a supercapacitor module, such as the supercapacitor module 400 or the energy storage apparatus 350, according to an embodiment. The set of graphs 800 include a first graph 810 of DC output voltage, measured in volts (V), as a function of DC output current, measured in amperes (A), as well as a second graph 820 of DC output power as a function of DC output current and a third graph 830 of DC input power as a function of DC output current.

The first graph 810 includes a plot of the output voltage 812 for a PDU with the supercapacitor module and a plot of the output voltage 814 for a PDU without the supercapacitor module. In particular, the first graph 810 shows the DC drop voltage on the PDU with a supercapacitor module is lower than the PDU without the supercapacitor module at the same DC output current. The second graph 820 includes a plot of the output power 822 for a PDU with the supercapacitor module and a plot of the output power 824 for a PDU without the supercapacitor module. The second graph 820 thus shows the output power 822 of the PDU with the supercapacitor module is more than the output power 824 for the PDU without the supercapacitor module at the same DC output current. The third graph 830 includes a plot of the input power 832 for a PDU with the supercapacitor module and a plot of the input power 834 for a PDU without the supercapacitor module. The third graph 830 shows the PDU with the supercapacitor module needs lower input power than the PDU without the supercapacitor module at the same DC output current.

As depicted, the output voltage 812 for the PDU with the supercapacitor module is higher than the output voltage 814 for the PDU without the supercapacitor module across all output currents. Similarly, the output power 822 for the PDU with the supercapacitor module is greater than the output power 824 for the PDU without the supercapacitor module across all output currents, though the relative increase in output power due to the supercapacitor module is more substantial for higher output currents. Notably, the input power 832 for the PDU with the supercapacitor module is substantially lower than the input power 834 for the PDU without the supercapacitor module across all output currents. Therefore, the use of a PDU with the supercapacitor module as described herein eliminates the need to upgrade electrical utilities of a hospital or other imaging site when an imaging system equipped with a high power x-ray generation system.

FIG. 9 shows a set of graphs 900 illustrating example electrical measurements for a first exposure 902 without a supercapacitor module, shown on the left side of the set of graphs 900, and a second exposure 904 with a supercapacitor module, shown on the right side of the set of graphs 900, according to an embodiment. As depicted, the first exposure 902 without the supercapacitor module occurs from time t1 to time t2, while the second exposure 904 with the supercapacitor module occurs from time t3 to time t4. The duration of both exposures 902 and 904 is the same, such that Δt=t2−t1=t4−t3 for both exposures 902 and 904. The set of graphs 900 includes a first graph 910 depicting a plot of DC voltage 912 over time, a second graph 920 depicting a plot of DC output current 922 over time, a third graph 930 depicting a plot of output power 932 over time, and a fourth graph 940 depicting a plot of supercapacitor voltage 942, a plot of supercapacitor state of charge percentage (SOC %) 944, and a plot of supercapacitor current 946 over time.

As depicted, the DC output current 922 and the output power 932 are the same for both the first exposure 902 and the second exposure 904. However, the voltage drop depicted by the voltage 912 is lower for the second exposure 904 than the first exposure 902 due to the supercapacitors. The lower voltage drop of the second exposure 904 indicates a higher efficiency from the use of a supercapacitor module in comparison to the lack of a supercapacitor module as described herein. Also, the low voltage drop of the second exposure 904 due to the supercapacitor module provides better and more stable performance for the x-ray generator for the x-ray tube.

Figure 10:
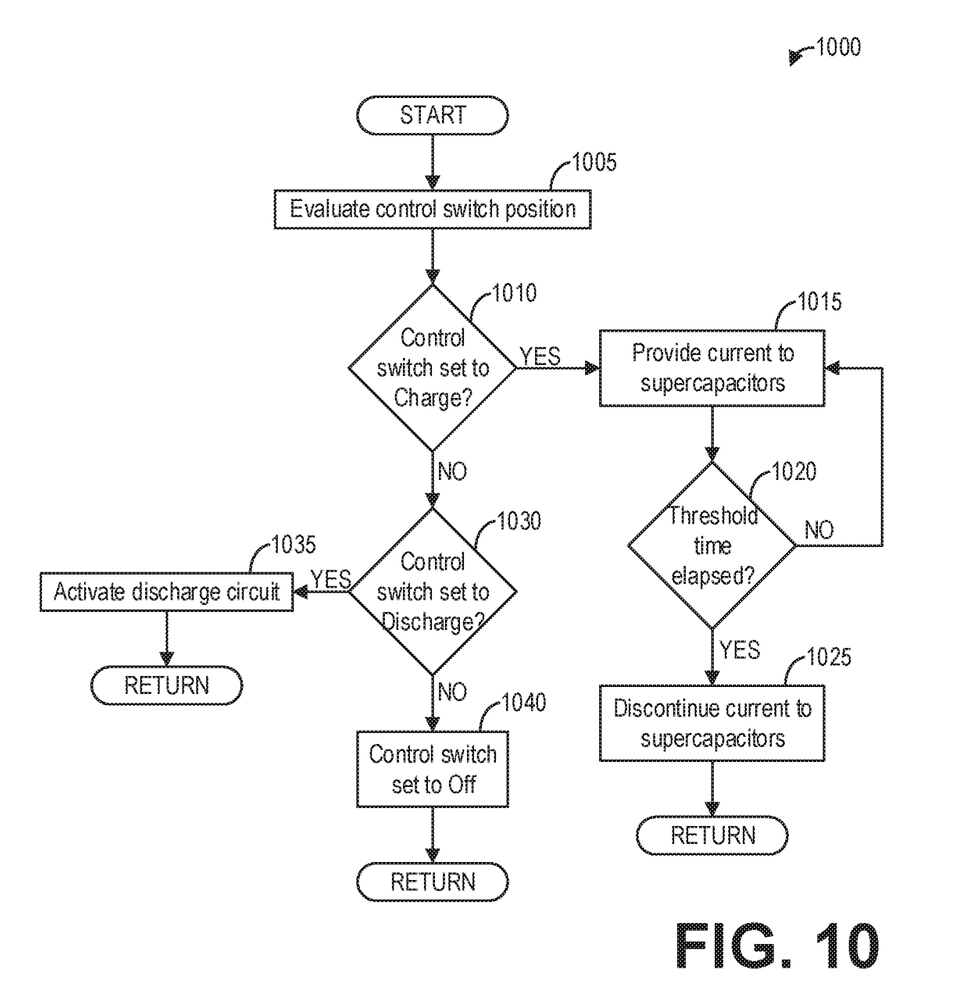
FIG. 10 shows a high-level flow chart illustrating an example method for controlling an energy storage apparatus according to an embodiment.

FIG. 10 shows a high-level flow chart illustrating an example method 1000 for controlling a supercapacitor module according to an embodiment. In particular, method 1000 relates to controlling a supercapacitor module, such as the energy storage apparatus 350 or supercapacitor module 400, configured as described hereinabove. Method 1000 begins at 1005. At 1005, method 1000 evaluates the position of the control switch, such as the control switch 450, of the supercapacitor module 400. As described hereinabove, the control switch 450 may include three positions, such as a first On position configured to Charge the supercapacitors 410, an Off position configured to disconnect electrical flow to the circuits of the supercapacitor module 400, and a second On position configured to Discharge the supercapacitors 410.

At 1010, method 1000 determines if the control switch is set to Charge. If the control switch is set to Charge ("YES"), method 1000 continues to 1015. At 1015, method 1000 provides current to the supercapacitors 410 to charge the supercapacitors 410. At 1020, method 1000 determines whether a threshold time has elapsed. Method 1000 may determine if the threshold time has elapsed based on a timer switch of the control circuit 430, such as the timer switch 615 of the control circuit 600. The threshold time may be predetermined based on the amount of time for charging the supercapacitors to a full capacity based on the input current. In some examples, the threshold time may comprise six or seven minutes, as an illustrative and non-limiting example. If the threshold time has not elapsed ("NO"), method 1000 continues providing current to the supercapacitors at 1015. Once the threshold time has elapsed ("YES"), the supercapacitors are charged and method 1000 continues to 1025. At 1025, method 1000 discontinues current to the supercapacitors. Method 1000 then returns.

Referring again to 1010, if the control switch is not set to Charge ("NO"), method 1000 continues to 1030. At 1030, method 1000 determines if the control switch is set to Discharge. If the control switch is set to Discharge ("YES"), method 1000 continues to 1035. At 1035, method 1000 activates the discharge circuit to discharge the supercapacitors. The discharge circuit may comprise, for example, the components of the control circuit 600 relating to discharging the supercapacitors. To that end, the switch 612 for the discharge contactor, for example, may be opened to activate the discharging of the supercapacitors. A timer switch, such as the switch 617, may open after a threshold discharge time, such as fifteen minutes, to automatically discontinue the discharging of the supercapacitors once the supercapacitors are discharged. The LEDs of the control circuit 600 may be configured to indicate to the user that discharging is occurring as well as when the discharging is complete. Method 1000 then returns.

However, if the control switch is not set to Discharge ("NO"), method 1000 continues to 1040, as the control switch is set to Off and no action is taken. Method 1000 then returns.

Thus, the energy storage apparatus 350 may be manually controlled via the control switch 450. When the control switch 450 is set to Charge, the energy storage apparatus 350 charges the supercapacitors 410 of the energy storage apparatus 350 and furthermore directly outputs the stored electrical energy of the supercapacitors 410 to the DC bus 310 when the desired power of the x-ray generator 320 and x-ray tube 322 exceeds the maximum power output of the PDU 305. When the control switch 450 is set to Discharge, the energy storage apparatus 350 discharges the supercapacitors 410 without powering any DC loads coupled to the DC bus 310. When the control switch 450 is set to Off, the energy storage apparatus 350 does not allow current flow to and from the circuitry of the energy storage apparatus.

Thus, apparatuses, systems, and methods are provided for powering an imaging system. In one embodiment, a system comprises a direct current (DC) bus, an x-ray source coupled to the DC bus, a power distribution unit (PDU) with an input coupled to a three-phase alternating current (AC) source and an output coupled to the DC bus, and an energy storage apparatus comprising a supercapacitor, the energy storage apparatus coupled to the DC bus and configured to store electrical energy output by the PDU in the supercapacitor, and output the stored electrical energy directly to the DC bus for powering the x-ray source.

In one example of the system, the energy storage apparatus outputs the stored electrical energy to the DC bus during at least an initial duration of an exposure of the x-ray source to assist the PDU in powering the x-ray source. In a second example of the system optionally including the first example, the energy storage apparatus further comprises a power circuit configured with soft start capacitors for gradually charging the supercapacitor. In a third example of the system optionally including one or more of the first and second examples, the energy storage apparatus comprises at least two supercapacitors including the supercapacitor. In a fourth example of the system optionally including one or more of the first through third examples, the supercapacitor stores the electrical energy when a positive contactor of the energy storage apparatus is connected, and a second supercapacitor of the at least two supercapacitors stores the electrical energy when a negative contactor of the energy storage apparatus is connected. In a fifth example of the system optionally including one or more of the first through fourth examples, the energy storage apparatus comprises a discharge circuit configured to discharge the stored electrical energy from supercapacitor without providing the stored electrical energy to the DC bus. In a sixth example of the system optionally including one or more of the first through fifth examples, the energy storage apparatus further comprises a control switch configured with a Charge position, an Off position, and a Discharge position, wherein the energy storage apparatus is configured to store the electrical energy in the supercapacitor responsive to the control switch positioned in the Charge position, activate the discharge circuit responsive to the control switch positioned in the Discharge position, and disable current flow within the energy storage apparatus responsive to the control switch positioned in the Off position. In a seventh example of the system optionally including one or more of the first through sixth examples, the energy storage apparatus further comprises at least one fan configured to selectively cool one or more resistors of the energy storage apparatus during charging and discharging of the supercapacitor. In an eighth example of the system optionally including one or more of the first through seventh examples, the energy storage apparatus does not include a converter for transferring DC power. In a ninth example of the system optionally including one or more of the first through eighth examples, the energy storage apparatus outputs the stored electrical energy to the DC bus when a desired input power for the x-ray source exceeds an output limit of the PDU. In a tenth example of the system optionally including one or more of the first through ninth examples, the system further comprises an x-ray generator coupled to the x-ray source and the DC bus for controlling the x-ray source, wherein the x-ray source is coupled to the DC bus via the x-ray generator.

In another embodiment, an apparatus for an imaging system comprises electrical terminals including at least a positive terminal and a negative terminal coupled to a direct current (DC) bus of the imaging system for receiving and outputting electrical energy, and at least one supercapacitor, wherein the at least one supercapacitor is configured to store electrical energy received by the electrical terminals from the DC bus, the at least one supercapacitor configured to directly output the stored electrical energy to the DC bus to assist a DC source in powering an x-ray source of the imaging system.

In a first example of the apparatus, the apparatus further comprises circuitry configured to control and power the at least one supercapacitor, the circuitry including soft start capacitors for gradually charging the at least one supercapacitor. In a second example of the apparatus optionally including the first example, the circuitry is further configured to selectively discharge the at least one supercapacitor without powering the x-ray source. In a third example of the apparatus optionally including one or more of the first and second examples, the apparatus further comprises a fan configured to selectively cool one or more components of the circuitry during charging and discharging of the at least one supercapacitor. In a fourth example of the apparatus optionally including one or more of the first through third examples, the at least one supercapacitor is configured to directly output the stored electrical energy to the DC bus when a desired power of the x-ray source exceeds a maximum output power of the DC source. In a fifth example of the apparatus optionally including one or more of the first through fourth examples, the apparatus further includes circuitry configured to protect the at least one supercapacitor, the circuitry including a current transducer sensor, a voltage sensor, at least a sensor configured to measure a temperature and a voltage balance of the at least one supercapacitor, and a field programmable gate array (FPGA). In a sixth example of the apparatus optionally including one or more of the first through fifth examples, the FPGA is configured to monitor a temperature of the at least one supercapacitor, a voltage balance of the at least one supercapacitor, an input voltage of the at least one supercapacitor, and a current of the at least one supercapacitor, and if one or more of the temperature, the voltage balance, the input voltage, and the current does not meet a predetermined condition relative to a respective threshold setting, the FPGA is configured to prevent charging of the at least one supercapacitor.

In yet another embodiment, a method for an imaging system comprises charging at least one supercapacitor of an energy storage apparatus coupled to a direct current (DC) bus with electrical energy converted from alternating current (AC) by a power distribution unit (PDU) coupled to the DC bus, and directly outputting the electrical energy stored in the at least one supercapacitor to the DC bus for powering an x-ray source of the imaging system coupled to the DC bus responsive to a desired power input for the x-ray source exceeding a maximum power output of the PDU.

In a first example of the method, the method further comprises powering the x-ray source solely with the PDU when the desired power input for the x-ray source is below the maximum power output of the PDU. In a second example of the method optionally including the first example, charging the at least one supercapacitor comprises gradually charging, with soft start circuitry, the at least one supercapacitor. In a third example of the method optionally including one or more of the first and second examples, the method further comprises discharging the at least one supercapacitor responsive to a control switch of the energy storage apparatus positioned at a Discharge position. In a fourth example of the method optionally including one or more of the first through third examples, a field programmable gate array (FPGA) monitors a temperature of the at least one supercapacitor, a voltage balance of the at least one supercapacitor, an input voltage of the at least one supercapacitor, and a current of the at least one supercapacitor, and if one or more of the temperature, the voltage balance, the input voltage, and the current does not meet a predetermined condition relative to a respective threshold setting, the FPGA is configured to prevent the charging of the at least one supercapacitor.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a direct current (DC) bus;
an x-ray generator coupled to the DC bus;
a power distribution unit (PDU) with an input coupled to a three-phase alternating current (AC) source and an output coupled to the DC bus; and
an energy storage apparatus comprising at least one supercapacitor, the energy storage apparatus coupled to the DC bus and configured to store electrical energy output by the PDU in the at least one supercapacitor, and output the stored electrical energy directly to the DC bus for powering the x-ray generator;
wherein the energy storage apparatus further comprises a power circuit configured with at least one soft start capacitor for gradually charging the at least one supercapacitor.

2. The system of claim 1, wherein the energy storage apparatus outputs the stored electrical energy to the DC bus during at least an initial duration of an exposure of an x-ray source coupled to the x-ray generator to assist the PDU in powering the x-ray generator.

3. The system of claim 1, wherein the at least one supercapacitor stores the electrical energy when a positive contactor of the energy storage apparatus is connected and when a negative contactor of the energy storage apparatus is connected.

4. The system of claim 1, wherein the energy storage apparatus comprises a discharge circuit configured to discharge the stored electrical energy from the at least one supercapacitor without providing the stored electrical energy to the DC bus.

5. The system of claim 4, wherein the energy storage apparatus further comprises a control switch configured with a charge position, an off position, and a discharge position, wherein the energy storage apparatus is configured to store the electrical energy in the at least one supercapacitor responsive to the control switch positioned in the charge position, activate the discharge circuit responsive to the control switch positioned in the discharge position, and disable current flow within the energy storage apparatus responsive to the control switch positioned in the off position.

6. The system of claim 1, wherein the energy storage apparatus further comprises at least one fan configured to selectively cool one or more resistors of the energy storage apparatus during charging and discharging of the at least one supercapacitor.

7. The system of claim 1, wherein the energy storage apparatus does not include a converter for transferring DC power.

8. The system of claim 1, wherein the energy storage apparatus outputs the stored electrical energy to the DC bus when a desired input power for the x-ray generator exceeds an output limit of the PDU.

9. An apparatus for an imaging system, comprising:
at least two electrical terminals including at least a one positive terminal and a at least one negative terminal coupled to a direct current (DC) bus of the imaging system for receiving and outputting electrical energy;
at least one supercapacitor, wherein the at least one supercapacitor is configured to store electrical energy received by the electrical terminals from the DC bus, wherein the at least one supercapacitor is configured to directly output the stored electrical energy to the DC bus to assist a DC power source in powering an x-ray generator of the imaging system; and
a circuit configured to control and power the at least one supercapacitor, the circuit including at least one soft start capacitor for gradually charging the at least one supercapacitor.

10. The apparatus of claim 9, wherein the circuit is further configured to selectively discharge the at least one supercapacitor without powering the x-ray generator.

11. The apparatus of claim 9, further comprising a fan configured to selectively cool one or more components of the circuit during charging and discharging of the at least one supercapacitor.

12. The apparatus of claim 9, wherein the at least one supercapacitor is configured to directly output the stored electrical energy to the DC bus when a desired power of the x-ray generator exceeds a maximum output power of the DC power source.

13. A method for an imaging system, comprising:
charging at least one supercapacitor of an energy storage apparatus coupled to a direct current (DC) bus with electrical energy converted from alternating current (AC) by a power distribution unit (PDU) coupled to the DC bus; and
directly outputting the electrical energy stored in the at least one supercapacitor to the DC bus for powering an x-ray generator of the imaging system coupled to the DC bus responsive to a desired power input for the x-ray generator exceeding a maximum power output of the PDU;
wherein a field programmable gate array (FPGA) monitors a temperature of the at least one supercapacitor, a voltage balance of the at least one supercapacitor, an input voltage of the at least one supercapacitor, and a current of the at least one supercapacitor, and wherein if one or more of the temperature, the voltage balance, the input voltage, and the current does not meet a predetermined value relative to a respective threshold value, the FPGA is configured to prevent the charging of the at least one supercapacitor.

14. The method of claim 13, further comprising powering the x-ray generator solely with the PDU when the desired power input for the x-ray generator is below the maximum power output of the PDU.

15. The method of claim 13, wherein charging the at least one supercapacitor comprises gradually charging the at least one supercapacitor with a soft start circuit.

16. The method of claim 13, further comprising discharging the at least one supercapacitor responsive to a control switch of the energy storage apparatus positioned at a discharge position.

* * * * *